US008022035B2

(12) United States Patent
Schwartz et al.

(10) Patent No.: US 8,022,035 B2
(45) Date of Patent: Sep. 20, 2011

(54) Y4 SELECTIVE RECEPTOR AGONISTS FOR THERAPEUTIC INTERVENTIONS

(75) Inventors: Thue Schwartz, Hoersholm (DK); Paul Brian Little, Hoersholm (DK); Lars-Ole Gerlach, Hoersholm (DK); Christian Elling, Hoersholm (DK)

(73) Assignee: 7TM Pharma A/S, Hoersholm (DK)

( * ) Notice: Subject to any disclaimer, the term of this patent is extended or adjusted under 35 U.S.C. 154(b) by 431 days.

(21) Appl. No.: 12/067,392

(22) PCT Filed: Sep. 21, 2005

(86) PCT No.: PCT/EP2005/010314
§ 371 (c)(1),
(2), (4) Date: Aug. 5, 2008

(87) PCT Pub. No.: WO2007/038942
PCT Pub. Date: Apr. 12, 2007

(65) Prior Publication Data
US 2009/0118178 A1 May 7, 2009

(51) Int. Cl.
*A61K 38/22* (2006.01)
*C07K 14/575* (2006.01)

(52) U.S. Cl. ........... 514/5.3; 514/6.9; 514/9.7; 530/324; 530/345

(58) Field of Classification Search .................. None
See application file for complete search history.

(56) References Cited

U.S. PATENT DOCUMENTS

| 5,604,203 | A | 2/1997 | Balasubramaniam |
|---|---|---|---|
| 5,830,434 | A | 11/1998 | Taylor et al. |
| 6,458,381 | B1 | 10/2002 | Sourovoi |
| 6,588,708 | B2 | 7/2003 | Wang |
| 2004/0214772 | A1 | 10/2004 | Quay |
| 2008/0255046 | A1 | 10/2008 | Schwartz |
| 2008/0261871 | A1 | 10/2008 | Schwartz |
| 2008/0269114 | A1 | 10/2008 | Schwartz |
| 2009/0186811 | A1 | 7/2009 | Schwartz |
| 2010/0160226 | A1 | 6/2010 | Schwartz |

FOREIGN PATENT DOCUMENTS

| WO | WO 92/07935 | 5/1992 |
|---|---|---|
| WO | WO 95/17906 | 7/1995 |
| WO | WO 98/11126 | 3/1998 |
| WO | WO 99/46283 | 9/1999 |
| WO | WO 02/47712 | 6/2002 |
| WO | WO 03/026591 | 4/2003 |
| WO | WO 2005/053726 | 6/2005 |
| WO | WO 2005/077094 | 8/2005 |
| WO | WO 2005/089786 | 9/2005 |
| WO | WO 2005/089789 | 9/2005 |
| WO | WO 2005/089790 | 9/2005 |
| WO | WO 2007/038942 | 4/2007 |
| WO | WO 2007/038943 | 4/2007 |
| WO | WO 2008/132435 | 11/2008 |
| WO | WO 2010/031521 | 3/2010 |

OTHER PUBLICATIONS

Bard et al., "Cloning and functional expression of a human Y4 subtype receptor for pancreatic polypeptide, neuropeptide Y, and peptide YY," *J. Biol. Chem.* 270, 26762-65, Nov. 10, 1995.

Cabrele et al., Y-receptor affinity modulation by the design of pancreatic polypeptide/neuropeptide Y chimera led to Y5-receptor ligands with picomolar affinity, *Peptides* 22, 365-78, Mar. 2001.
Kurtzhals et al., "Albumin binding of insulins acylated with fatty acids: Characterization of the ligand-protein interaction and correlation between binding affinity and timing of the insulin effect in vivo," Biochem. J. 312, 725-31, 1995.
Sheffield, "Modification of clearance of therapeutic and potentially therapeutic proteins," Current Drug Targets, Cardiovascular and Haematological Disorders, vol. 1, 1022, Jun. 2001.
International Search Report and Written Opinion for PCT/EP2005/010314, mailed Mar. 27, 2006.
Asakawa et al., "Characterization of the Effects of Pancreatic Polypeptide in the Regulation of Energy Balance," Gastroenterology 124, 1325-36, 2003.
Balasubramanian et al., "Syntheses and Receptor Affinities of Partial Sequences of Peptide YY (PYY)," *Peptide Res.* 1, Sep. 1988.
Batterham et al., "Gut Hormone PYY3-36 Physiologically Inhibits Food Intake," *Nature* 418, 650-54, Aug. 8, 2003.
Batterham et al., "Pancreatic Polypeptide Reduces Appetite and Food Intake in Humans," *J. Clin. Endocrinol. Metab.* 88, 3989-92, Aug. 2003.
Berntson et al., "Pancreatic Polypeptide Infusions Reduce Food Intake in Prader-Willi Syndrome," *Peptides* 14, 4970503, 1993.
Dumont et al., "Characterization of a new neuropeptide Y Y5 agonist radioligand: [<125>I][cPP(1-7), NYP(19-23), Ala<31>, Aib<32>, Gln<34>]hPP," Neuropeptides, vol. 38, No. 4, pp. 163-174, Aug. 2004.
Eberlein et al., "A New Molecular Form of PYY: Structural Characterization of Human PYY (3-36) and PYY (1-36)," *Peptides* 10, 797-803, 1989.
Félétou et al., "Neuropeptide Y2 receptors as drug targets for the central regulation of body weight," Current Opinion in Investigational Drugs, vol. 6, No. 10, pp. 1002-1011, Oct. 2005.
Fuhlendorff J et al: "The anti parallel pancreatic polypeptide fold in the binding of neuropeptide Y to Y-1 and Y-2 receptors" Jul. 15, 1990, Journal of Biological Chemistry, American Society of Biological Chemists, Baltimore, MD, US, pp. 11706-11712, XPQ02339077 ISSN: 0021-9258.
Gehlert et al., "Characterization of the Peptide Binding Requirements for the Cloned Human Pancreatic Polypeptide-Preferring Receptor," *Mol. Pharmacol.* 50i, 112-18, 1996.
Gerald et al., "Expression Cloning and Pharmacological Characterization of a Human Hippocampal Neuropeptide Y/Peptide YY Y2 Receptor Subtype," J. Biol. Chem. 270, 26758-61, 1995.
Grundemar, "Characterization of the Receptor Response for the Neuropeptide Y-Evoked Suppression of Parasympathetically-Mediated Contractions in the Guinea Pig Trachea," *Regulatory Peptides* 71, 97-101, 1997.

(Continued)

*Primary Examiner* — Jeffrey E Russel
(74) *Attorney, Agent, or Firm* — Banner & Witcoff, Ltd.

(57) ABSTRACT

Y4 receptor agonist peptide selected from the group consisting of: [Ala30]PP$_{2-36}$, [Thr30]PP$_{2-36}$, [Asn30]PP$_{2-36}$, [Gln30]PP$_{2-36}$, [Glu10]PP$_{2-36}$, [Glu10,Leu17,Thr30]PP$_{2-36}$, [Nle17,Nle30]PP$_{2-36}$, [Glu10,Nle17,Nle30]PP$_{2-36}$, their PP$_{1-36}$ equivalents, and analogues and derivatives thereof as described in the specification, are selective agonists of the Y4 receptor relative to the Y1 and Y2 receptors, and are useful in the treatment, for example, of obesity and overweight, and conditions in which these are considered contributory factors, and in the treatment of diarrhoea and intestinal hypersecretion.

69 Claims, No Drawings

OTHER PUBLICATIONS

Jorgensen et al., "Structure-function studies on neuropeptide Y and pancreatic polypeptide: Evidence for two PP-fold receptors in vas deferens," *Eur. J. Pharmacol.* 186, 105-14, 1990.

Katsuura et al., "Roles of Pancreatic Polypeptide in Regulation of Food Intake," *Peptides 23*, 323-29, 2002.

Keire et al., "Structure and receptor binding of PYY analogs," Peptides, vol. 23, No. 2, pp. 305-321, Feb. 2002.

Kirby et al., "Defining Structural Requirements for Neuropeptide Y Receptors Using Truncated and Conformationally Restricted Analogues," *J. Med. Chem. 36*, 385-93, 1993.

Larsen et al., "The Neuropeptide Y_Y4/ Receptor is Highly Expressed in Neurones of the Rat Dorsal Vagal Complex," *Mol. Brain Res. 48*, 1-6, 1997.

Lerch et al., "Bovine Pancreatic Polypeptide (bPP) Undergoes Significant Changes in Conformation and Dynamics upon Binding to DPC Micelles," *J. Mol. Biol. 322*, 1117-33, 2002.

Lerch et al., "Structural Similarities of Micelle-bound Peptide YY (PYY) and Neuropeptide Y (NPY) are Related to their Affinity Profiles at the Y Receptors," *J. Mol. Biol. 339*, 1153-68, Jun. 18, 2004.

Mccrea et al., "2-36[K ,RYYSA$^{19-23}$]PP a novel Y5-receptor preferring ligand with strong stimulatory effect on food intake," *Regulatory Peptides 87*, 47-58, Feb. 2000.

Medeiros & Turner, "Post-Secretory Processing of Regulatory Peptides: the Pancreatic Polypeptide Family as a Model Example," *Biochemie 76*, 283-87, 1994.

Murase et al., "Acylation of the a Group in Neuropeptide Y(12-36) Increases Binding Affinity for the $Y_2$ Receptor," *Abstr. J. Biochem (Tokyo) 119*, 37-41, 1996.

Nygaard et al., "The PP-Fold Solution Structure of Human Polypeptide YY and Human PYY3-36 as Determined by NMR," *Biochem. 45*, 8350-57, 2006.

Parker et al., "GR231118 (1229U91) and other analogs of the C-terminus of neuropeptide Y are potent neuropeptide Y Y1 receptor antagonists and neuropeptide Y Y4 receptor agonists," *Eur. J. Pharmacol.* 349, 97-105, 1998.

Rossi et al., "Central nervous system neuropeptides involved in obesity," Handbook of Exp. Pharmacol. 149, 313-41, 2000.

Walker et al., "A Structure-Activity Analysis of the Cloned Rat and Human Y4 Receptors for Pancreatic Polypeptide[1,2]," *Peptides 18*, 609-12, 1997.

Walker et al., "Peptide Receptor Structure and Function I," *Soc. Neuroscience Abs. 21*, 1012, Nov. 11, 1995.

Walker et al., "Binding of NPY8 PYY and PP Analogs to cloned human Y2 and Y4 receptors" Society for Neuroscience Abstracts, Society for Neuroscience, US, vol. 21, No. 1/3 Nov. 11, 1995.

UnitProt Accession No. P01298, Apr. 3, 2007.

U.S. Appl. No. 12/597,090, filed Oct. 22, 2009 (unpublished).

Yao Shenggen et al., "Stabilization of the Helical Structure of Y2-Selective Analogues of Neuropeptide Y by Lactam Bridges," *J. Med. Chem. 45*, 2310-18, May 23, 2002.

International Search Report and Written Opinion for PCT/GB2008/001379, Sep. 15, 2009.

Unpublished U.S. Appl. No. 13/062,932, filed Mar. 8, 2011.

Y4 SELECTIVE RECEPTOR AGONISTS FOR THERAPEUTIC INTERVENTIONS

CROSS REFERENCE TO RELATED APPLICATIONS

This application is a National Stage application of co-pending PCT application PCT/EP2005/010314 filed Sep. 21, 2005, which is incorporated herein by reference in its entirety.

This application incorporates by reference the contents of an 11.5 kb text file created on May 31, 2011 and named "12067392.txt,"
which is the sequence listing for this application.

FIELD OF THE INVENTION

The invention relates to peptide or peptidic compounds that act as selective agonists of the Y4 relative to the Y1 and Y2 receptors, and to their use in treatment of conditions responsive to activation of Y4 receptors, for example in treatment of obesity and overweight, and conditions in which these are considered contributory factors, and in the treatment of diarrhoea and intestinal hypersecretion.

BACKGROUND TO THE INVENTION

The PP-fold family of peptides—NPY (Neuropeptide Y) (human sequence—SEQ ID. No:1), PYY (Peptide YY) (human sequence—SEQ ID. No:2), and PP (Pancreatic Polypeptide) (human sequence—SEQ ID. No:3), are naturally secreted homologous, 36 amino acid, C-terminally amidated peptides, which are characterized by a common three-dimensional, structure—the PP-fold—which is surprisingly stable even in dilute aqueous solution and is important for the receptor recognition of the peptides.

NPY is a very wide-spread neuropeptide with multiple actions in various parts of both the central and peripheral nervous system acting through a number of different receptor subtypes in man: Y1, Y2, Y4 and Y5. The main NPY receptors are the Y1 receptor, which generally is the post-synaptic receptor conveying the "action" of the NPY neurones and the Y2 receptor which generally is a pre-synaptic, inhibitory receptor. This is also the case in the hypothalamus, where NPY neurones—which also express the melanocortin receptor antagonist/inverse agonist AgRP (agouti related peptide)—act as the primary "sensory" neurones in the stimulatory branch of the arcuate nucleus. Thus, in this the "sensor nucleus" for the control of appetite and energy expenditure, the NPY/AgRP neurones together with the inhibitory POMC/CART neurones monitor the hormonal and nutritional status of the body as these neurones are the target for both the long-term regulators such as leptin and insulin and short term regulators such as ghrelin and PYY (see below). The stimulatory NPY/AgRP neurones project for example to the paraventricular nucleus—also of the hypothalamus—where its postsynaptic target receptors are believed to be Y1 and Y5 receptors. NPY is the most potent compound known in respect of increasing food intake, as rodents upon intracerebroventricular (ICV) injection of NPY will eat until they literally burst. AgRP from the NPY/AgRP neurones acts as an antagonist mainly on melanocortin receptors type 4 (MC-4) and block the action of POMC derived peptides—mainly aMSH—on this receptor. Since the MC4 receptor signal acts as an inhibitor of food intake, the action of AgRP is—just like the NPY action—a stimulatory signal for food intake (i.e. an inhibition of an inhibition). On the NPY/AGRP neurons are found inhibitory—pre-synaptic—Y2 receptors, which are the target both of locally released NPY as well as a target for the gut hormone PYY—another PP-fold peptide.

PYY is released during a meal—in proportion to the calorie content of the meal—from entero-endocrine cells in the distal small intestine and the colon, to act both in the periphery on GI-tract functions and centrally as a satiety signal. Peripherally, PYY is believed to function as an inhibitor—an "illeal break"—on for example upper GI-tract motility, gastric acid and exocrine pancreatic secretion. Centrally, PYY is believed to act mainly on the presynaptic, inhibitory Y2 receptors on the NPY/AgRP neurones in the arcuate nucleus, which it is believed get access to from the blood (Batterham et al. 2002 *Nature* 418: 650-4). The peptide is released as PYY1-36, but a fraction—approximately 50%—circulates as PYY3-36 which is a product of degradation by dipeptidylpeptidase-IV an enzyme which removes a dipeptide from the N-terminus of a peptide provided that a Pro or Ala is found in position two as in all three PP-fold peptides—PP, PYY and NPY (Eberlein et al. 1989 *Peptides* 10: 797-803). Thus PYY in the circulation is a mixture of PYY1-36, which acts on both Y1 and Y2 receptors (as well as Y4 and Y5 with various affinities), and PYY3-36—which has lower affinities for the Y1, Y4 and Y5 receptors than for the Y2 receptor.

PP is a hormone, which is released from endocrine cells in the pancreatic islets, almost exclusively governed by vagal cholinergic stimuli elicited by especially food intake (Schwartz 1983 *Gastroenterology* 85:1411-25). PP has various effects on the gastrointestinal tract, but none of these are observed in isolated cells and organs, and all appear to be dependent on an intact vagal nerve supply (Schwartz 1983 *Gastroenterology* 85:1411-25). In accordance with this, the PP receptors, which are called Y4 receptors, are located in the brain stem with a strong expression in vagal motor neurones—activation of which results in the peripheral effects of PP—and in the nucleus tractus solitarirus (NTS)—activation of which results in the effects of PP as a satiety hormone (Whitecomb et al. 1990 *Am. J. Physiol.* 259: G687-91, Larsen & Kristensen 1997 *Brain Res. Mol. Brain Res* 48: 1-6). It should be noted that PP from the blood has access to this area of the brain since the blood brain barrier is "leaky" in this area where various hormones from the periphery are sensed. Recently it has been argued that part of the effect of PP on food intake is mediated through an action on neurones—especially the POMC/CART neurones in the arcuate nucleus (Batterham et al. 2004 *Abstract* 3.3 *International NPY Symposium in Coimbra, Portugal*). PP acts through Y4 receptors for which it has a subnanomolar affinity as opposed to PYY and NPY which have nanomolar affinity for this receptor (Michel et al. 1998 *Pharmacol. Rev.* 50: 143-150). PP also has an appreciable affinity for the Y5 receptor, but it is not likely of physiological importance in relation to circulating PP due to both lack of access to the cells in the CNS where this receptor especially is expressed and due to the relatively low affinity for PP.

PP-Fold Peptide Receptors

There are four well established types of PP-fold peptide receptors in man: Y1, Y2, Y4, and Y5 which all recognize NPY1-36 and PYY1-36 with similar affinity. At one time a Y3 receptor type, which might prefer NPY over PYY, was suggested, but today this is not accepted as a real receptor subtype (Michel et al. 1998 *Pharmacol. Rev.* 50: 143-150). A Y6 receptor subtype has been cloned, which in man is expressed in a truncated form lacking TM-VII as well as the receptor tail and consequently at least on its own does not appear to form a functional receptor molecule.

Y1 receptors—affinity studies suggest Y1 binds NPY and PYY equally well and basically not PP.

Y2 receptors—affinity studies suggest Y2 binds NPY and PYY equally well and basically not PP.

Y4 receptors—affinity studies suggest that Y4 binds PP with subnanomolar affinity corresponding to the concentrations found in plasma whereas NPY and PYY are recognized with much lower affinity.

Y5 receptors—affinity studies suggest that Y5 binds NPY and PYY equally well, and also binds PP with lower affinity, which however is below the normal circulating levels of this hormone. PYY3-36 is also recognized well by the Y5 receptor, however this receptor is to a large degree expressed in the CNS where such peptide cannot get access to the receptor readily when administered in the periphery.

PP-fold peptides and analogs of these have been suggested for use in the treatment of obesity and associated diseases, including for example Prader Willi's syndrome, based on the demonstrated effects of certain of the these peptides in animal models and in man and on the fact that obese people have low basal levels of PP and PYY as well as lower meal responses of these peptides (Holst J J et al. 1983 *Int. J. Obes.* 7: 529-38; Batterham et al. 1990 *Nature*). It has been known since the mid seventies that PP could affect food intake in rodents. In 1993 it was reported that infusion of PP in morbidly obese patients with Prader Willi's syndrome decreased food intake (Berntson et al. 1993 *Peptides* 14: 497-503). Recently this effect of PP was confirmed by infusion of PP in normal human subjects where a long lasting suppression of appetite and reduced food intake over 24 hours was observed (Bafferham et al 2003, *Clin. Endocrinol. Metab.* 88: 3989-92).

For the treatment of conditions responsive to Y4 receptor modulation, such as obesity and intestinal hyper-secretion it would therefore be desirable to use PP-fold peptides or PP-fold peptide mimics, which acted as agonists and were specific for the Y4 receptor intended as target, and which stably preserve elements of the PP-fold structure important for receptor binding. In particular, it would be highly desirable to use such agents which are selective for the Y4 receptor over the Y1 and Y2 receptors. This is particularly important, since activation of the Y1 receptor is expected to potentially cause unwanted cardiovascular and renal side effects such as vasoconstriction and natriuresis Moreover, activation of the Y2 receptor may also cause side effects. Although it is still unclear what the really efficient angiogenic Y receptor profile is, Y2 agonists such as NPY3-36 apparently can induce revascularization in for example ischemic hind limb models, i.e. when administered in high doses with constant exposure as for example released from inoperated pellets (Zukowska Z et al. *Trends Cardiovasc Med.* 2003, 13:86-92). The angiogenic response to NPY is reduced in Y2 receptor knock out animals; however, the response to this broad-spectrum Y receptor agonist NPY is in fact not eliminated and both Y2 and Y5 receptors are up-regulated in ischemic vessels (Lee et al *J. Clin. Invest.* 2003, 111: 1853-62). Nevertheless, a PP-fold peptide or PP-fold peptide mimic could through activation of the Y2 receptor cause side effects such as worsen the retinopathy for example in diabetic patients and could potentially aid in the neovascularization associated with the growth of certain cancers. Thus use of efficacious and selective Y4 receptor over Y1 and Y2 receptor agonists would be particularly useful in diseases and conditions susceptible to Y4 receptor activation. Our co-pending International patent application no PCT/EP2005/002983, the contents of which are hereby incorporated by reference, relates to a class of Y receptor agonists which are selective for the Y4 receptor over the Y1 and Y2 receptors, and to some specific members of that class.

This invention relates to specific peptides which are highly selective for the Y4 receptor over the Y1 and Y2 receptors.

DETAILED DESCRIPTION OF THE INVENTION

According to the invention, there is provided a peptide selected from the group consisting of:

(i) [Ala30]$PP_{2-36}$ (SEQ ID No: 4) and [Ala30]PP (SEQ ID No: 5)

(ii) [Thr30]$PP_{2-36}$ (SEQ ID No: 6) and [Thr30]PP (SEQ ID No: 7)

(iii) [Asn30]$PP_{2-36}$ (SEQ ID No: 8) and [Asn30]PP (SEQ ID No: 9)

(iv) [Gln30]$PP_{2-36}$ (SEQ ID No: 10) and [Gln30]PP (SEQ ID No: 11)

(v) [Glu10]$PP_{2-36}$ (SEQ ID No: 12) and [Glu10]PP (SEQ ID No: 13)

(vi) [Glu10, Leu17, Thr30]$PP_{2-36}$ (SEQ ID No: 14) and [Glu10,Leu17,Thr30]PP (SEQ ID No: 15)

(vii) [Nle17, Nle30]$PP_{2-36}$ (SEQ ID No: 16) [Nle17,Nle30]PP (SEQ ID No: 17)

(viii) [Glu10,Nle17,Nle30]$PP_{2-36}$ (SEQ ID No: 18) and [Glu10,Nle17,Nle30]PP (SEQ ID No: 19) and analogues thereof which are (a) conservatively substituted in one or more positions other than position 30 in the case of (i)-(iv), or position 10 in the case of (v), or positions 17 and 30 in the case of (vii), or positions 10, 17 and 30 in the case of (vi) and (viii); and/or (b) N-terminally acylated, PEGylated, or covalently coupled to a serum albumin binding motif, a glycosaminoglycan binding motif or a helix inducing motif, said covalent coupling being to a residue of the peptide or to a residue substituted in peptide which provides a functional group for such covalent binding.

The notation PP used herein refers to the PP sequence (SEQ ID No:3). Thus [Ala30]PP (SEQ ID No: 5) has the human PP sequence (SEQ ID No: 3) but with alanine substituted for leucine at position 30 thereof.

The notation $PP_{2-36}$ used herein refers to the PP sequence (SEQ ID No:3) but with the first N-terminal amino acid (Ala) deleted. However, the position numbering of $PP_{2-36}$ is by reference to the full length PP (SEQ ID No:3). Thus, the peptide [Ala30]$PP_{2-36}$ (SEQ ID No: 4) has the human PP sequence SEQ ID No:3, but with Ala1 deleted, and alanine substituted for leucine at position 30 of SEQ ID No:3.

The eight peptide pairs and their analogues of the invention are Y receptor agonists which are highly selective for the Y4 receptor over the Y1 and Y2 receptors when measured by the potency assay described herein. The peptides of the invention are grouped in pairs, since the defined substitutions in the truncated $PP_{2-36}$ background produce essentially the same Y4 selectivity relative to Y1 and Y2 as the same substitutions in the full length PP background.

In the PP sequence Asp 10 is particularly prone to cyclisation in solution to form a cyclic imidate which ring opens to form mixtures of the α and β-aspartate with concomitant scrambling of stereochemistry. In peptide pairs (v), (vi) and (viii) of the invention that residue has been replaced by Glu. This substitution preserves the special electrostatic potential distribution within the peptides and thereby the overall stability of the peptide as well as its solubility. Since Glu in position 10 does not undergo analogous cyclisation/ring opening to form γ-Glu it has the beneficial effect of improving the bulk and the solution stability of the peptide as a pharmaceutical agent compared to its Asp 10 counterparts. Improved solution stability leads to increased synthetic yields and reduces the requirement for troublesome, costly and waste producing purification of the desired product from the closely related β-Asp impurity.

The Met 17 and Met 30 residues in the normal PP sequence can potentially undergo oxidation upon storage in solution. In all the peptides listed above Met 30 has been substituted with a residue that is not prone to this alteration. In peptide pairs (vii) and (viii) of the invention Met17 has been replaced by Nle which prevents oxidation at this position and preserves the aliphatic side chain structure as Nle is a bio-isostere for Met.

The existence of the Ala1-Pro2 motif in the normal PP sequence confers upon that peptide an inherent instability towards the β-ketopiperazine degradation pathway in which the terminal amino function can 'bite back' via a 6 membered transition state that is stabilized by the turn inducing Pro, and undergo an intramolecular transamidation at the site of the proline carboxamide function leading to the formation of β-ketopiperazine and PP3-36. This pathway leads to—degradation products formed on storage of the lyophilates, and significant degradation in solutions of peptides containing the Ala1-Pro2 sequence. Thus in a preferred embodiment of the invention this is prevented by removal of Ala1 from the PP sequence, i.e. all the analogs of $PP_{2-36}$ listed above. This has the beneficial effect of improving the stability of these peptides both in solution and as lyophilates and therefore improving their properties as pharmaceuticals.

The various stability improving modifications presented above, taken singly or together represent a significant advance in the pharmaceutical properties of these peptides. Improved stability both during synthesis, leading to higher yields and less purification, and prolonged shelf life of the lyophilate and the solutions of these peptides reduces significantly the environmental burden of the production (and reducing the necessity for remanufacture) of peptides of this invention by reducing the use of raw materials, solvents, utilities and therefore also the production of waste products.

In this specification, reference is made to amino acids by their common names or abbreviations, such as valine (Val), leucine (Leu), isoleucine (Ile), methionine (Met), phenylalanine (Phe), asparagine (Asn), glutamic acid (Glu), glutamine (Gln), histidine (His), lysine (Lys), arginine (Arg), aspartic acid (Asp), glycine (Gly), alanine (Ala), serine (Ser), threonine (Thr), tyrosine (Tyr), tryptophane (Trp), cysteine (Cys) and proline (Pro). When referred to by its common name or abbreviation, without specifying its steroisomeric form, the amino acid in question is to be understood as the L-form.

The term "conservative substitution" as used herein denotes that one or more amino acids is replaced by another, biologically similar residue. Examples include substitution of amino acid residues with similar characteristics, e.g. small amino acids, acidic amino acids, polar amino acids, basic amino acids, hydrophobic amino acids and aromatic amino acids. Non-limiting examples of conservative amino acid substitutions suitable for use in the present invention include those in the following Table and analogous substitutions of the original residue by non-natural alpha amino acids which have similar characteristics. For example, in a preferred embodiment of the invention Met residues are substituted with norleucine (Nle) which is a bioisostere for Met, but which—as opposed to Met—is not readily oxidised. Another example of a conservative substitution with a residue normally not found in endogenous, mammalian peptides and proteins would be the conservative substitution of Arg or Lys with for example, ornithine, canavanine, aminoethylcysteine or other basic amino acid. For further information concerning phenotypically silent substitutions in peptides and proteins, see, for example, Bowie et al. *Science* 247, 1306-1310, 1990.

| Original residue | Conservative substitution |
|---|---|
| Ala | Gly |
| Arg | Lys |
| Asn | Gln, His, Thr |
| Asp | Glu |
| Gln | Asn, His |
| Glu | Asp |
| His | Asn, Gln |
| Ile | Leu, Val |
| Leu | Ile, Val |
| Lys | Arg |
| Met | Leu, Ile |
| Phe | Tyr, Trp, His |
| Ser | Thr, Asn |
| Thr | Ser, Asn, Gln |
| Trp | Tyr, Phe, His |
| Tyr | Trp, Phe, His |
| Val | Ile, Leu |

Conservatively substituted analogues of the invention may have, for example, up to 10 conservative substitutions, or in another embodiment up to 5, or in yet another embodiment 3 or fewer.

N-Acylated Analogues

The removal of Ala1 from the PP sequence as in the various analogs of $PP_{2-36}$ of the invention eliminates the susceptibility towards dipeptidyl peptidase IV (DPP-IV), and towards other amino peptidases in particular aminopeptidase P, due to the new N-terminal proline residue, In addition, all eight pairs of the Y4 selective agonists with which the invention is concerned may be acylated at their N-terminus to confer resistance to other aminopeptidases. For example, acylation may be with a carbon chain having from 2 to 24 carbon atoms, and N-terminal acetylation is a particular example.

Analogues with Covalently Bound Functional Motifs

Various modifications may be made to the eight agonist pairs of the invention, for the purpose of improving their pharmacokinetics, pharmacodynamics and metabolic properties. Such modifications may involve linking the agonist to functional groupings (also known as motifs) known per se in the art of peptidic or proteinaceous pharmaceuticals. Three particular modifications of particular benefit in the case of the agonists with which the invention is concerned, are linkage with serum albumin binding motifs, or glycosaminoglycan (GAG) binding motifs, or PEGylation.

Serum-Albumin Binding Motifs

Serum albumin binding motifs are typically lipophilic groups, incorporated to enable a prolonged residence in the body upon administration or for other reasons, which may be coupled in various known ways to peptidic or proteinaceous molecules, for example i) via a covalent linkage to e.g. a functional group present on a side-chain amino acid residue, ii) via a functional group inserted in the peptide or in a suitable derivatized peptide, iii) as an integrated part of the peptide. For example, WO 96/29344 (Novo Nordisk A/S) and P. Kurtzhals et al. 1995 Biochemical J. 312: 725-31, describe a number of suitable lipophilic modifications which can be employed in the case of the agonists with which this invention is concerned.

Suitable lipophilic groups include optionally substituted, saturated or unsaturated, straight or branched hydrocarbon groups of from 10 to 24 carbon atoms. Such groups may form, or may form part of, a side chain to the backbone of the agonist, for example by ether, thioether, amino, ester or amide linkage to a side chain of an amino acid residue in the backbone, or to a backbone carbon or a branch from a backbone carbon of a non-peptidic linker radical in the backbone of a PP-fold mimic agonist. The chemistry strategy for attachment of the lipophilic group is not critical, but the following side chains including lipophilic groups are examples which can be linked to a backbone carbon of the agonist, or suitable branch therefrom:

$CH_3(CH_2)_n CH(COOH)NH-CO(CH_2)_2 CONH-$, wherein n is an integer from 9 to 15, $CH_3(CH_2)_r CO-NHCH(COOH)(CH_2)_2 CONH-$, wherein r is an integer from 9 to 15, $CH_3(CH_2)_s CO-NHCH((CH_2)_2 COOH)CONH-$, wherein s is an integer from 9 to 15, $CH_3(CH_2)_m CONH-$, wherein m is an integer from 8 to 18, $-NHCOCH((CH_2)_2 COOH)NH-CO(CH_2)_p CH_3$, wherein p is an integer from 10 to 16, $-NHCO(CH_2)_2 CH(COOH)NH-CO(CH_2)_q CH_3$, wherein q is an integer from 10 to 16, $CH_3(CH_2)_n CH(COOH)NHCO-$, wherein n is an integer from 9 to 15, $CH_3(CH_2)_{p'} NHCO-$, wherein p' is an integer from 10 to 18, $-CONHCH(COOH)(CH_2)_4 NH-CO(CH_2)_m CH_3$, wherein m is an integer from 8 to 18, $-CONHCH(COOH)(CH_2)_4 NH-COCH((CH_2)_2 COOH)NH-CO(CH_2)_p CH_3$, wherein p is an integer from 10 to 16, $-CONHCH(COOH)(CH_2)_4 NH-CO(CH_2)_2 CH(COOH)NH-CO(CH_2)_q CH_3$, wherein q is an integer from 10 to 16, and a partly or completely hydrogenated cyclopentanophenanthrene skeleton.

In one chemical synthetic strategy the lipophilic group-containing side chain is a $C_{12}$, $C_{14}$, $C_{16}$ or $C_{18}$ acyl group, for example a tetradecanoyl group, acylating an amino group present in the side chain of a residue of the backbone of the agonist.

As stated, the modification of agonists for use in accordance to provide improved serum binding characteristics is a strategy which may be applied in general, and particularly in the case of the specific agonists listed above. Thus suitable modified agonists include [N—(N'-tetradecanoyl)-gammagluatamoyl-Lys13,Ala30]PP$_{2-36}$ and [Glu10,N—(N'-hexadecanoyl)-gammagluatamoyl-Lys13,Leu17,Thr30]PP$_{2-36}$ and conservatively substituted analogues thereof.

GAG Binding

As in the case of lipophilic serum binding motifs discussed above, the agonists with which this invention are concerned may be modified by incorporation of the GAG binding motif as, or as part of, a side chain to the backbone of the agonist. Known GAG-binding motifs for incorporation in this way include the amino acid sequences XBBXBX and/or XBBBXXBX, wherein B is a basic amino acid residue and X is any amino acid residue. A plurality, for example three, of such sequences may be incorporated in a concatameric (straight chain) or dendrimeric (branched chain) fashion. Specific concatameric GAG motifs include Ala-Arg-Arg-Arg-Ala-Ala-Arg-Ala-Ala-Arg-Arg-Arg-Ala-Ala-Arg-Ala (SEQ ID NO:20), and Ala-Arg-Arg-Arg-Ala-Ala-Arg-Ala-Ala-Arg-Arg-Arg-Ala-Ala-Arg-Ala-Ala-Arg-Arg-Arg-Ala-Ala-Arg-Ala (SEQ ID NO:21) (both of which may, for example be coupled through an amide bond formed between the C-terminus of the concatameric GAG-binding motif and an amino group in the side chain of a backbone amino acid of the agonist, such as the epsilon amino group of Lys13 in the agonist [Lys13,Ala30]PP2-36 or [Glu10,Lys13, Leu17, Thr30]PP2-36.

Instead of being attached to the agonist as, or as part of a side chain to a backbone residue, the GAG motif may be covalently linked to the C- or (preferably) N-terminus of the agonist, either directly or via a linker radical. Here also the GAG-binding motif may comprise the amino acid sequence XBBXBX and/or XBBBXXBX, wherein B is a basic amino acid residue and X is any amino acid residue, for example the sequence [XBBBXXBX]$_n$ where n is 1 to 5, B is a basic amino acid residue and X is any amino acid residue. Such concatameric repeats tend to form alpha helices when they bind to GAG's, and consequently when fused to the C-terminal hexapeptide/last alpha helical turn, can stabilise that turn and thereby present the combined structure in an optimal way for Y4 receptor recognition. Specific examples of agonists of this type are [XBBBXXBX-XBBBXXBX]PP or [XBBBXXBX-XBBBXXBX-XBBBXXBX]PP, wherein B is a basic amino acid residue and X is any amino acid residue, particularly Ala-Arg-Arg-Arg-Ala-Ala-Arg-Ala-Ala-Arg-Arg-Arg-Ala-Ala-Arg-Ala-Ala-Arg-Arg-Arg-Ala-Ala-Arg-Ala-[Ala30]PP2-36 (SEQ ID NO:22).

The Y4 selective agonists with which the present invention is concerned are useful, inter alia, in indications for which prolonged exposure is desirable. For such indications in particular, the agonists preferably comprise a glycosamino glycan (GAG) binding motif as discussed above. Such motifs ensure that the agonists bind to GAGs in the extracellular matrix, and thereby ensures prolonged local exposure of the Y4 receptors in that tissue. Growth factors, chemokines etc bind to GAGs through patches of basic amino acids, which interact with the acidic sugars of the GAGs. These positively charged epitopes on the growth factors are usually composed of side chains from basic residues, which are not necessarily located consecutively in sequence but are often presented in close proximity by a secondary structural element such as an a-helix or a turn or by the overall three dimensional structure of the protein. Certain GAG-binding, linear sequences, discussed above, have been described, for example XBBXBX and XBBBXXBX where B represents a basic residue (Hileman et al. Bioassays 1998, 20: 156-67). These segments have been shown by circular dichroism to form α-helices upon binding to GAGs. If such sequences are placed for example in a concatameric or dendrimeric construct where for example three such sequences are presented—for example each as a ARRRAARA sequence (SEQ ID NO:23)—the resulting 24-mer peptide—for example ARRRAARA-ARRRAARA-ARRRAARA (SEQ ID NO:21)—ensures a retention in the extracellular matrix similar to high molecular weight polylysine, i.e. it is not washed out during a 4 hour perfusion period (Sakharov et al. FEBS Lett 2003, 27: 6-10).

Thus Growth factors and chemokines are naturally constructed with two types of binding motifs: one binding motif for the receptor through which signal transduction is achieved and one binding motif for GAG's through which attachment and long-lasting local activity is achieved. Peptides such as PYY and NPY are neuropeptides and hormones, which are rather rapidly washed out of the tissue and are not optimized for long-lasting local activity. By attaching a GAG-binding motif to a Y4 selective agonist according to the present invention—a bi-functional molecule similar to the growth factors and chemokines is constructed having both a receptor binding epitope in the PP-fold peptide part and a GAG-binding motif. An example of such an agonist is [N-{(Ala-Arg-Arg-Arg-Ala-Ala-Ala-Arg-Ala)3}-Lys13,Ala30]PP2-36(SEQ ID NO:24).

PEGylation

In PEGylation, a polyalkyleneoxide radical or radicals, is/are covalently coupled to peptidic or proteinaceous drugs to improve effective half life in the body following administration. The term derives from the preferred polyalkyleneoxide used in such processes, namely that derived from ethylene glycol—polyethyleneglycol, or "PEG".

A suitable PEG radical may be attached to the agonist by any convenient chemistry, for example via a backbone amino acid residue of the agonist. For instance, for a molecule like e.g. PEG, a frequently used attachment group is the epsilon-amino group of lysine or the N-terminal amino group. Other attachment groups include a free carboxylic acid group (e.g. that of the C-terminal amino acid residue or of an aspartic acid or glutamic acid residue), suitably activated carbonyl groups, mercapto groups (e.g. that of a cysteine residue), aromatic acid residues (e.g. Phe, Tyr, Trp), hydroxy groups (e.g. that of Ser, Thr or OH-Lys), guanidine (e.g. Arg), imidazole (e.g. His), and oxidized carbohydrate moieties.

When the agonist is PEGylated it usually comprises from 1 to 5 polyethylene glycol (PEG) molecules such as, e.g. 1, 2 or 3 PEG molecules. Each PEG molecule may have a molecular weight of from about 5 kDa (kiloDalton) to about 100 kDa, such as a molecular weight of from about 10 kDa to about 40 kDa, e.g., about 12 kDa or preferably no more than about 20 kDa. In a particular embodiment of the invention, PEG 40 kDa (otherwise designated PEG40000) is the PEGylating agent.

Suitable PEG molecules are available from Shearwater Polymers, Inc. and Enzon, Inc. and may be selected from SS-PEG, NPC-PEG, aldehyde-PEG, mPEG-SPA, mPEG-SCM, mPEG-BTC, SC-PEG, tresylated mPEG (U.S. Pat. No. 5,880,255), or oxycarbonyl-oxy-N-dicarboxylmide-PEG (U.S. Pat. No. 5,122,614).

Particular examples of PEGylated agonists of the invention are [N-PEG5000-Lys13,Ala30]PP2-36 and [Glu10,N-PEG5000-Lys13,Leu17,Thr30]PP2-36 and [N-PEG20000Lys13]PP2-36, [N-PEG2000Lys13]PP2-36 and [N-PEG40000Lys13]PP2-36.

Serum Albumin, GAG and PEG

Whether the modification to the agonist is attachment of a group to facilitate serum binding, GAG binding or improved stability via PEGylation, the serum albumin binding motif or GAG binding motif, or PEG radical may be, or may form part of, a side chain of a backbone carbon of the agonist corresponding to any of the following positions 1, 3, 6, 7, 10, 11, 12, 13, 15, 16, 18, 19, 21, 22, 23, 25, 26, 28, 29, and 32, although in the case of peptides [Glu10]PP$_{2-36}$ and [Glu10,Leu17,Thr30]PP$_{2-36}$ position 10 is not available.

Conjugation to Larger Biomolecules

The selective Y4 receptor agonists may be used as fusion proteins where they are linked for example to albumin or another protein or carrier molecule which provides beneficial pharmacokinetic or other types of properties such as for example decreased renal elimination. There are multiple chemical modifications and linkers which can be used for such a covalent attachment as known in the art, just as there are multiple proteins or carriers which can be used. Especially covalent attachment of the selective Y4 peptide agonist to albumin is preferred and at one of the positions in the PP-fold structure, which have been pointed out elsewhere herein in relation to modifications with the various motifs. Such fusion proteins can be produced through various semi-synthetic techniques where the peptide may be made through peptide synthesis as described herein and the biomolecule through recombinant technology. The fusion protein may also be made enterely as a recombinant molecule expressed for example as a precursor molecule extended by a Gly-Lys-Arg sequence, which when expressed as a secretory protein in eukaryotic cells will be cleaved by biosynthetic enzymes and the Gly turned into the carboxyamide on the C-terminal Tyr residue of the C-terminal Y4 receptor recognition sequence.

Helix Inducing Peptides

Acylation of the N-terminus of the agonists with which the invention is concerned has been mentioned as a means of stabilising the agonist against the action of aminopeptidases. Another stabilising modification involves the covalent attachment of a stabilizing peptide sequence of 4-20 amino acid residues covalently at the N- and/or the C-terminus, preferably the N-terminus. The amino acid residues in such a peptide are selected from the group consisting of Ala, Leu, Ser, Thr, Tyr, Asn, Gln, Asp, Glu, Lys, Arg, His, Met and the like. In an interesting embodiment the N-terminal peptide attachment comprises 4, 5 or 6 Lys residues, for example Lys-Lys-Lys-Lys-Lys-[Ala30]PP2-36 (SEQ ID NO:25). These can be linked at the N-terminus of the PP-fold peptide agonist. A general description of such stabilizing peptide extensions is given in WO 99/46283 (Zealand Pharmaceuticals), which is hereby incorporated by reference.

The receptor agonists with which the invention is concerned may be prepared by well-known methods such as, e.g., a synthetic, semisynthetic and/or recombinant method. The methods include standard peptide preparation techniques such as, e.g., solution synthesis, and solid-phase synthesis. Based on textbook and general knowledge within the field, a person skilled in the art knows how to proceed in order to obtain the agonists and derivatives or modifications thereof.

Clinical Indications

The Y4-specific agonists with which the invention is concerned are of value in the treatment of conditions responsive to activation of Y4 receptors. Such conditions include those for which regulation of energy intake or energy metabolism is indicated. For any such use, the agonist may be one which comprises a modification or motif which confers stability towards peptidases, serum protein binding properties, PEGylation or GAG-binding motif to prolong serum and/or tissue half-life.

Diseases or conditions in which regulation of energy intake or energy metabolism is indicated include obesity and overweight, and conditions in which obesity and overweight are considered contributory factors, such as bulimia, bulimia nervosa, Syndrome X (metabolic syndrome), diabetes, type 2 diabetes mellitus or Non Insulin Dependent Diabetes Mellitus (NIDDM), hyperglycemia, insulin resistance, impaired glucose tolerance, cardiovascular disease, hypertension, atherosclerosis, coronary artery disease, myocardial infarction, peripheral vascular disease. stroke, thromboembolic diseases, hypercholesterolemia, hyperlipidemia, gallbladder disease, osteoarthritis, sleep apnea, reproductive disorders such as polycystic ovarian syndrome, or cancer of the breast, prostate, or colon.

Y4 selective agonists are also of value in the treatment of diarrhoea or hyper-secretion from intestinal stomia, and in the treatment of nausea or emesis, or as anti-nausea or antiemetic agents or co-treatment with drugs prone to cause nausea and/or emesis.

1. Obesity and Overweight

It was suggested already in the seventies that PP might be involved in the control of food intake. Recently, much evidence from rodent studies has accumulated showing very clearly that PP is in fact a powerful and efficient anorexigenic peptide when administered peripherally (Asakawa et al. Peptides 1999, 20; 1445-8; Katsuura et al. Peptides 2002, 23: 323-9; Asakawa et al. Gastroenterology 2003, 124: 1325-36). Since PP has no effect on appetite, food intake etc. in Y4 knock out animals it is very likely that PP acts through the Y4 receptor to reduce appetite and food intake (Batterham et al. 2004 abstract S3.3 from International NPY symposium in Coimbra Portugal). PP also has effect on food intake in diet induced obese animals. PP receptors have been found especially in the brain stem in area postreama and on vagal motor neurones where the blood brain barrier is not efficient and where circulating hormones such as PP can get access to the neurones. Thus it is very likely that the Y4 receptors in the NTS in the brain stem are a major target through which PP acts to suppress appetite and food intake. However, recent evidence also points to the possibility that PP may also act through Y receptors in the arcuate nucleus conceivably on the POMC and perhaps also the NPY/AgRP neurones (Batterham et al. Coimbra NPY meeting abstract S3.3). Low levels of PP are found in obese subjects especially Prader-Willi syndrome (Zipf et al. J. C. E. M. 1981, 52: 1264-6, Holst et al 1983, Int. J. Obes. 7: 529-38, Glaser et al Horm. Metab. 1988, 20: 288-92) and high PP levels are found in patients with anorexia nervosa. Importantly, infusion of PP in man decreases appetite and food intake for up to 24 hours (Batterham et al. JCEM 2003, 88: 3989-92). Thus, the effect of PP on food intake was observed after the PP levels in the circulation had returned to normal levels. Such long lasting effects on appetite etc, is well know from other compounds for example also from ICV injection of AgRP. Importantly infusion of PP has been shown to decrease food intake in mobidly obese patients with Prader Willi syndrome (Berntson et al 1993 Peptides 14: 497-503).

Hence, the Y4 selective agonists with which the invention is concerned are suitable for use in a subject, such as a mammal including a human, in order to regulate the energy intake. Accordingly, the invention relates to methods for altering energy intake, food intake, appetite, and energy expenditure. A method is disclosed herein for reducing energy or food intake by administering to a subject a cosmetically or therapeutically effective amount of such an agonist. In one embodiment, administration of the receptor agonist results in a decrease in the amount, either the total weight or the total volume or calorie content of the food. In another embodiment, it may result in a decrease of the intake of a food component, such as a decrease in the ingestion of lipids, carbohydrates, cholesterol, or proteins. In any of the methods disclosed herein, the preferred compounds that have been discussed in details herein could be administered. In an additional embodiment, a method is disclosed herein for reducing appetite by administering a therapeutically effective amount of such an agonist. Appetite can be measured by any means known to one of skill in the art.

For example, decreased appetite can be assessed by a psychological assessment. In such an embodiment, administration of the receptor agonist results in a change in perceived hunger, satiety, and/or fullness. Hunger can be assessed by any means known to one of skill in the art. In one embodiment, hunger is assessed using psychological assays, such as by an assessment of hunger feelings and sensory perception using e.g. a questionnaire.

In a further embodiment, a method is disclosed herein for decreasing the motility of the upper GI tract as for example decreasing gastric emptying. PP, the prototype Y4 agonist, is known to decrease gastric emptying. The method includes administering a therapeutically effective amount of a Y4 selective agonist of the invention to the subject, thereby decreasing GI-tract motility. It is well known that compounds which decrease gastric emptying will have a beneficial effect in also decreasing food intake as the subject is feeling more full or satiated.

In a further embodiment, a method is disclosed herein for altering energy metabolism in a subject. The method includes administering a therapeutically effective amount of an agonist of the invention to the subject, thereby altering energy expenditure.

Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat. In a further embodiment a method is disclosed herein for any and all manipulations of the arcuate circuitry described in this application, which alter food intake coordinately and reciprocally alter energy expenditure. Energy expenditure is a result of cellular metabolism, protein synthesis, metabolic rate, and calorie utilization. Thus, in this embodiment, peripheral administration results in increased energy expenditure, and decreased efficiency of calorie utilization. In one embodiment, a therapeutically effective amount of a receptor agonist according to the invention is administered to a subject, thereby increasing energy expenditure.

In several embodiments both relating to the therapeutic use and to the cosmetic use, a Y4 selective agonist of the invention can be used for weight control and treatment, reduction or prevention of obesity, in particular any one or more of the following: preventing and reducing weight gain; inducing and promoting weight loss; and reducing obesity as measured by the Body Mass Index. As mentioned above, the invention also relates to the use of a Y4 selective agonist of the invention for controlling any one or more of appetite, satiety and hunger, in particular any one or more of the following: reducing, suppressing and inhibiting appetite; inducing, increasing, enhancing and promoting satiety and sensations of satiety; and reducing, inhibiting and suppressing hunger and sensations of hunger. The disclosure further relates to the use of a Y4 selective agonist of the invention in maintaining any one or more of a desired body weight, a desired Body Mass Index, a desired appearance and good health.

In a further or alternative aspect, the invention relates to a method for the treatment and/or prevention of reduced energy metabolism, feeding disorders, appetite disorders, overweight, obesity, bulimia, bulimia nervosa, Syndrome X (metabolic syndrome), or complications or risks associated thereto including diabetes, type 2 diabetes mellitus or Non Insulin Dependent Diabetes Mellitus (NIDDM), hyperglycemia, insulin resistance, impaired glucose tolerance, cardiovascular disease, hypertension, atherosclerosis, congestive heart failure, stroke, myocardial infarct, thromboembolic diseases, hypercholesterolemia, hyperlipidemia, gallbladder disease, osteoarthritis, sleep apnea, reproductive disorders such as polycystic ovarian syndrome, cancers of the breast, prostate, and colon, the method comprising administering to a subject such as a mammal including a human, an effective dose of one or more of a Y4 selective agonists as described herein.

2. Intestinal Hypersecretion

PP is know to have a strong anti-secretory effect on both the small and large intestine and this appears to be mediated through Y4 receptors located on the epithelial cells (Cox & Tough 2001 Br. J. Pharmacol. 135: 1505-12). It has been shown in vivo that peripheral administration of PYY—another PP-fold peptide activating Y1 and Y2 receptors—can cause a long-lasting reduction in intestinal secretion induced by vasoactive intestinal polypeptide in human subjects with ileostomies (Playford et al 1990 Lancet 335: 1555-57). It was concluded that PYY could be a therapeutic agent against diarrhoea. However, for example the natriuretic and hypertensive effects of the combined Y1 and Y2 agonists, NPY and PYY peptides have prevented this. Such side effects will not be relevant for the selective Y4 receptor agonists of the present invention. Thus the selective Y4 agonists of the present invention are particularly useful for the treatment or protection against hyper-secretion of the GI-tract including various forms of diarrhoea whether or not they directly are caused by hyper-secretion as a suppression of the intestinal secretion will either eliminate the cause of the diarrhoea or eliminate the symptoms. One particularly interesting indication is the hyper-secretion observed in patients with ileostomia, who often are losing large amounts of fluid. The selective Y4 agonists of the present invention are particularly useful for the treatment or protection against hypersecretion associated with small intestinal ileo-stomia.

3. Emesis and Nausea

Many peptides and other types of compounds which have been suggested as agents to control appetite, such as for example PYY and CB1 antagonists are know to be emetic. For example, PYY was in fact discovered—for "the second time"—in 1989 as the biologically active entity in an intestinal extract causing dogs to vomit (Harding and McDonald 1989 Peptides 10: 21-24). It was concluded that PYY was the most potent, circulating emetic peptide identified and that this effect was mediated through area postreama known to have a leaky blood brain barrier. It has also been reported that PYY3-36 can cause nausea when administered peripherally to human subjects (Nastech press release 29$^{th}$ of Jun. 2004). Interestingly, it was noted that PP given in similar doses did not cause vomiting in these dogs (Harding and McDonald 1989). Thus, PP which acts through Y4 receptors also located in the area postreama of the brain stem—does not cause emesis or vomiting. Importantly, large doses of a combined Y2-Y4 agonist peptide—which has similar in vitro potency for the Y2 receptors as PYY—can be administered to animals such as cyno monkeys reaching very high plasma levels of 12-13.000 nM without observing any vomiting of the animals or evidence of GI-tract side effects This lack of emesis is surprising since PYY3-36 which has a similar potency on the Y2 receptor does cause emesis in man and conceivably in animals when administered at much lower doses. Thus, surprisingly the combined Y2-Y4 selective agonist does not cause emesis to the same degree as the selective Y2 agonist—PYY3-36 compound—does. Apparently, Y4 receptor activation—conceivably in the area postreama—prevents the emetic effect of the Y2 activation in this case an effect caused by the same compound acting on the Y2 receptors. Thus, the Y4 selective compounds of the present invention are particularly useful for the treatment or protection against emesis and nausea. This will be emesis and nausea associated with the treatment of for example another appetite suppressive agent for example of the Y2 agonist type, the CB1 antagonist/inverse agonist type or other types of appetite suppressive agents, which often cause emesis and nausea. It should be noted that the appetite suppressive effect of the Y4 selective compounds very likely will be additive or even synergistic at the same time. Thus, by co-administering a Y4 selective agonist of the present invention together with another appetite suppressive or other type of anti-obesity agent, two goals are achieved: 1) the beneficial effect of obtaining a fully or partial additive antiobesity effect, 2) the beneficial effect of the Y4 selective compound eliminating or diminishing the emetic effect of the other anti-obesity agent.

The Y4 selective compounds of the present invention are also particularly useful for the treatment or protection against emesis and nausea associated with pregnancy. For this particular indication it is important that the Y4 selective compounds are close analogs of natural PP-fold peptides and generally are expected to have negligible side effects. Especially the fact that these peptides do not in the placenta cross from the maternal circulation into the fetal circulation is important since this will give minimal exposure of the fetus and thereby very low risk of causing developmental side effects.

The Y4 selective compounds of the present invention, and PP itself, are also useful for the treatment or protection against emesis and nausea associated with alcohol intolerance 4. Irritable Bowl Disease The secretion and function of the natural ligand for the Y4 receptor, PP is highly correlated to the activity of the autonomous nervous system (Schwartz 1983, Gastroenterology 85:1411-25). Thus for example fluctuations in the plasma levels of PP are closely correlated to fluctuations in GI-tract motility and secretions and to secretion of the hormone/neurotransmitter motilin. PP is known to work through activation of the parasympathetic nerveous system and through the central vagal control centers such as the vagal motor neurones in the brain stem and thereby controlling the activity in the efferent vagal fibers to the GI tract. Since irritable bowl disease is believed to be associated with malfunctions in especially the GI-tract motility and function leading to pain etc. and malfunction in the control of this through the autonomic nervous system, the use of the selective Y4 agonists in the treatment of irritable bowl disease is a preferred embodiment of the present invention Additional Comments Concerning Administration of Y4 Agonists for the Treatment or Prevention of Obesity and Related Diseases During a meal a large repertoire of gastrointestinal hormones and neurotransmitter systems are activated in a carefully concerted, sequential and overlapping manner. Moreover, food components influence not only the secretion of GI hormones and the activity of various afferent neuronal pathways but these food components also influence various hormones and centers in the CNS directly after they are absorbed. Thus the regulation of food intake and energy expenditure is a highly complex and multifaceted process. In view of this it is surprising that certain hormones such as PP in fact can substantially affect the system when administered in a way which results in, for example only 3-4 times the plasma levels which are achieved during a meal.

Administrations of such compounds—Y4 selective agonists—apparently mainly have the intended effect if the compounds are given in the fasting state in an effective dose as described. If the Y4 agonists are given in a situation where the various hormonal and neuronal systems are active due to the presence of food components in the GI tract or the expectation of a meal, the effect is not seen or a smaller effect is observed. Thus, in a preferred embodiment of the invention the selective Y4 agonist is administered in the fasting state in an effective dose either sub-cutaneously, nasally or through other means as described elsewhere herein. In the present context, the term "fasted state" means that the subject has not eaten any food or drink within at least the last 2 hours before administration of the Y2 receptor agonist such as, e.g., within at least the last 3 hours, within at least the last 4 hours, within at least the last 5 hours, within at least the last 6 hours, within at least the last 7 hours, within at least the last 8 hours, within at least the last 9 hours, within at least the last 10 hours, within at least the last 11 hours or within at least the last 12 hours before dosing.

In a subgroup of the population, Y4 agonists may not have the intended action due to genetic variations such as polymorphisms in the Y4 receptor gene. Loss of function mutations in these receptors are likely to be associated with obesity. Thus, in a preferred embodiment of the invention an analysis of the Y4 gene of the subject to be treated is performed in order to probe for polymorphisms/mutations in these genes and identification of such polymorphisms. Based on such an analysis an optimal treatment of the subjects can be made. For example, only subjects with normal genotype or with polymorphisms, which do not affect the function of Y4 agonists, should be treated with such agonists. Another possibility is to increase the dose of the Y4 agonist in subjects who express an impaired receptor in order to ensure an optimal effect of the drug. In the case where the obesity of a subject is caused by an impairment in the function of the Y4 receptor it could be argued that treatment with a—for example large doses—of a Y4 agonist is a form of replacement therapy—provided that at least some of the relevant receptor function is still left—for example in heterozygote patients.

In one embodiment of the invention an acute test may be performed where a Y4 agonist is administered to ensure that these compounds have the intended effect in the subject to be treated before a chronic treatment is started. Through these means it is ensured that only subjects who are susceptible to treatment with Y4 agonists are treated with these compounds.

Dosages

The therapeutically effective amount of a Y4 receptor agonist according to the invention will be dependent on specific agonist employed, the age, weight and condition of subject being treated, the severity and type of the condition or disease being treated, the manner of administration and the strength of the composition applied.

For example, a therapeutically effective amount of a Y4 receptor agonist thereof can vary from about 0.01 µg per kilogram (kg) body weight to about 1 g per kg body weight, such as about 1 µg to about 5 mg per kg body weight, or about 5 µg to about 1 mg per kg body weight. In another embodiment, the receptor agonist is administered to a subject at 0.5 to 135 picomole (pmol) per kg body weight, or about 72 pmol per kg body weight.

In one specific, non-limiting example from about 5 to about 50 nmol is administered as a subcutaneous injection, such as from about 2 to about 20 nmol, or about 1.0 nmol is administered as a subcutaneous injection. The exact dose is readily determined by one skilled in the art based on the potency of the specific compound (such as the receptor agonist) utilized, the age, weight, sex and physiological condition of the subject. The dose of an agonist can be a molar equivalent of the therapeutically effective dose of PYY3-36.

The amounts can be divided into one or several doses for administration daily, every second day, weekly, every two weeks, monthly or with any other suitable frequency. Normally, the administration is once or twice daily.

Methods of Administration

The Y4 receptor agonist as well as cosmetic or pharmaceutical compositions according to the invention can be administered by any route, including the enteral (e.g. oral administration) or parenteral route. In a specific embodiment, the parenteral route is preferred and includes intravenous, intraarticular, intraperitoneal, subcutaneous, intramuscular, intrasternal injection and infusion as well as administration by the sublingual, transdermal, topical, transmucosal including nasal route, or by inhalation such as, e.g., pulmonary inhalation. In specific embodiments, the subcutaneous and/or the nasal administration route is preferred.

When administered centrally, the natural Y4 selective peptide PP may, as do NPY and PYY when administered ICV, induce eating (probably dye to activation of central receptors which normally are not reached by the circulating hormones or peripherally administered peptide compounds). Thus in cases where increased eating is to be avoided, it is preferred that the Y4 selective agonists of the invention are administered peripherally.

The receptor agonists can be administered as such dispersed in a suitable vehicle or they can be administered in the form of a suitable pharmaceutical or cosmetic composition. Such compositions are also within the scope of the invention. In the following are described suitable pharmaceutical compositions. A person skilled in the art will know how that such composition may also be suitable for cosmetic use or he will know how to adjust the compositions to cosmetic compositions by use of suitable cosmetically acceptable excipients.

Pharmaceutical Compositions

The receptor agonists (also denoted "compounds") according to the invention for use in medicine or cosmetics are normally presented in the form of a pharmaceutical composition comprising the specific compound or a derivative thereof together with one or more physiologically or pharmaceutically acceptable excipients.

The compounds may be administered to an animal including a mammal such as, e.g., a human by any convenient administration route such as, e.g., the oral, buccal, nasal, ocular, pulmonary, topical, transdermal, vaginal, rectal, ocular, parenteral (including inter alia subcutaneous, intramuscular, and intravenous cf. above), route in a dose that is effective for the individual purposes. A person skilled in the art will know how to chose a suitable administration route. As mentioned above, the parenteral administration route is preferred. In a specific embodiment, the receptor agonists are administered subcutaneously and/or nasally. It is well known in the art that subcutaneous injections can be easily self-administered.

A composition suitable for a specific administration route is easily determined by a medical practitioner for each patient individually. Various pharmaceutically acceptable carriers and their formulation are described in standard formulation treatises, e.g., Remington's Pharmaceutical Sciences by E. W. Martin.

The pharmaceutical composition comprising a compound according to the invention may be in the form of a solid, semi-solid or fluid composition. For parenteral use, the composition is normally in the form of a fluid composition or in the form of a semi-solid or solid form for implantation.

Fluid compositions, which are sterile solutions or dispersions can utilized by for example intravenous, intramuscular, intrathecal, epidural, intraperitoneal or subcutaneous injection of infusion. The compounds may also be prepared as a sterile solid composition, which may be dissolved or dispersed before or at the time of administration using e.g. sterile water, saline or other appropriate sterile injectable medium.

The fluid form of the composition may be a solution, an emulsion including nano-emulsions, a suspension, a dispersion, a liposomal composition, a mixture, a spray, or a aerosol (the two latter types are especially relevant for nasal administration).

Suitable mediums for solutions or dispersions are normally based on water or pharmaceutically acceptable solvents e.g. like an oil (e.g. sesame or peanut oil) or an organic solvent like e.g. propanol or isopropanol. A composition according to the invention may comprise further pharmaceutically acceptable excipients such as, e.g., pH adjusting agents, osmotically active agents e.g. in order to adjust the isotonicity of the composition to physiologically acceptable levels, viscosity adjusting agents, suspending agents, emulsifiers, stabilizers, preservatives, antioxidants etc. A preferred medium is water.

Compositions for nasal administration may also contain suitable non-irritating vehicles such as, e.g., polyethylene glycols, glycofurol, etc. as well as absorption enhancers well known by a person skilled in the art (e.g. with reference to Remington's Pharmaceutical Science)

For parenteral administration, in one embodiment the receptor agonists can be formulated generally by mixing it at the desired degree of purity, in a unit dosage injectable form (solution, suspension, or emulsion), with a pharmaceutically acceptable excipient or carrier, i.e., one that is non-toxic to recipients at the dosages and concentrations employed and is compatible with other ingredients of the composition.

Generally, the formulations are prepared by contacting the receptor agonist uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes. Due to the amphiphatic nature of the peptides described herein suitable forms also include micellar formulations, liposomes and other types of formulations comprising one or more suitable lipids such as, e.g., phospholipids and the like.

Preferably, they are suspended in an aqueous carrier, for example, in an isotonic buffer solution at a pH of about 3.0 to about 8.0, preferably at a pH of about 3.5 to about 7.4, 3.5 to 6.0, or 3.5 to about 5. Useful buffer substances include acetate, citrate, phosphate, borate, carbonate such as, e.g., sodium citrate-citric acid and sodium phosphate-phosphoric acid, and sodium acetate/acetic acid buffers.

The compositions may also be designed to controlled or prolonged delivery of the receptor agonist after administration in order to obtain a less frequent administration regimen. Normally a dosage regimen including 1-2 daily administrations is considered suitable, but within the scope of the present invention is also included other administration regimens such as, e.g., more frequent and less frequent. In order to achieve a prolonged delivery of the receptor agonist, a suitable vehicle including e.g. lipids or oils may be employed in order to form a depot at the administration site from which the receptor agonist is slowly released into the circulatory system, or an implant may be used. Suitable compositions in this respect include liposomes and biodegradable particles into which the receptor agonist has been incorporated.

In those situations where solid compositions are required, the solid composition may be in the form of tablets such as, e.g. conventional tablets, effervescent tablets, coated tablets, melt tablets or sublingual tablets, pellets, powders, granules, granulates, particulate material, solid dispersions or solid solutions.

A semi-solid form of the composition may be a chewing gum, an ointment, a cream, a liniment, a paste, a gel or a hydrogel.

Other suitable dosages forms of the pharmaceutical compositions according to the invention may be vagitories, suppositories, plasters, patches, tablets, capsules, sachets, troches, devices etc.

The dosage form may be designed to release the compound freely or in a controlled manner e.g. with respect to tablets by suitable coatings.

The pharmaceutical composition may comprise a therapeutically effective amount of a compound according to the invention.

The content of a compound of the invention in a pharmaceutical composition of the invention is e.g. from about 0.1 to about 100% w/w of the pharmaceutical composition.

The pharmaceutical compositions may be prepared by any of the method well known to a person skilled in pharmaceutical formulation.

In pharmaceutical compositions, the compounds are normally combined with a pharmaceutical excipient, i.e. a therapeutically inert substance or carrier.

The carrier may take a wide variety of forms depending on the desired dosage form and administration route.

The pharmaceutically acceptable excipients may be e.g. fillers, binders, disintegrants, diluents, glidants, solvents, emulsifying agents, suspending agents, stabilizers, enhancers, flavours, colors, pH adjusting agents, retarding agents, wetting agents, surface active agents, preservatives, antioxidants etc. Details can be found in pharmaceutical handbooks such as, e.g., Remington's Pharmaceutical Science or Pharmaceutical Excipient Handbook.

The following examples describe the preparation and activities of some specific agonists of the invention.

Syntheses

Peptidic agonists of the invention may be synthesized by solid phase peptide synthesis, using either an automated peptide synthesizer, or traditional bench synthesis. The solid support can be, for example, chlorotrityl (Cl) or Wang (OH) resin, both of which are readily available commercially. The active groups of those resins react readily with the carboxyl group of an N-Fmoc amino acid, thereby covalently binding it to the polymer. The resin-bound amine may be deprotected by exposure to piperidine. A second N-protected amino acid may then be coupled to the resin-amino acid. These steps are repeated until the desired sequence is obtained. At the end of the synthesis, the resin-bound protected peptide may be deprotected and cleaved from the resin with trifluoroacetic acid (TFA). Examples of reagents facilitating the coupling new amino acids to the resin-bound amino acid chain are: tetra-methyluronium hexafluorophosphate (HATU), O-(1H-benzotriazole-1-yl)-N,N,N',N'-tetramethyluronium hexafluorophosphate (HBTU), O-(1H-benzotriazole-1-yl)-N,N,N',N'-tetramethyluronium tetrafluoroborate (TBTU), 1H-hydroxybenzotriazole (HOBt).

Peptide synthesis by solution chemistry rather than solid phase chemistry is also feasible.

The peptides referred to herein were made by solid phase synthesis, on PAL Peg-PS resin, (amide resin (amide resin Applied Bioscience, Warrington, UK GEN913401), using Fmoc chemistry with a 5× reagent excess. The coupling was performed by HCTU throughout, solvent DMF. Fmoc removal was performed with 20% piperidine in DMF, 10-15 minutes. However, these peptides could just as well have been synthesised by various other standard peptide synthesis methods such as tBOC chemistry and solution chemistry instead of solid state etc. The synthesis is illustrated by the following description, but the other peptides with which the invention is concerned are made by similar methods:

```
Synthesis of [Ala30]PP2-36 (SEQ ID No: 4)
In general side group protection were standard
Fmoc except for:
Arg =                    Fmoc Arg(Pbf)-OH Asn, Gln =               Fmoc Asn(Trt)-OH Thr, Ser, Asp, Glu, Tyr = tButyl Ala-Ser 22-23 =          Fmoc AlaSer
                         pseudoproline
```

The peptide was synthesized by solid phase synthesis, on PAL Peg-PS resin (a resin which will generate the biologically important carboxyamide group upon cleavage), using Fmoc chemistry with a 5 fold molar reagent excess. The coupling was performed by HCTU throughout using DMF as solvent. Fmoc removal after each coupling step was performed with 20% piperidine in DMF for 10-15 minutes. The coupling was checked after each step by quantitative ninhydrin (Kaiser) assay. In certain cases double couplings could be performed.

The resin can be divided into parts to produce separate batches of peptide.

The peptides are cleaved of the resin with TFA, silane and water 94:3:3. The solvent was removed by a stream of nitrogen and the residue was washed with ether and air dried, dissolved in 10% acetic acid and freeze dried.

In one example of a purification method the crude material is purified by reverse phase HPLC using ACE 300A C18 columns, typically 250 mm×10 mm flow 2 ml/min, with 215 nm detection.
Buffer A=0.05% TFA in water
Buffer B=60% MeCN+0.05% TFA and water A typical gradient used for the sequences included herein is a gradient of 20% to 90% buffer B over 20 mins collect the main peak. Peptide identify is confirmed by mass spectroscopy using for example MALDI TOF ionisation technique (Electrospray or Atmospheric Pressure Chemical Ionisation techniques are other examples of ionisation techniques that can be used). Purity is checked by for example analytical HPLC method A. Fractions containing the product are pooled and freeze dried to yield the trifluoroacetate salt of the peptide product.

As mentioned, the other peptides with wich the invention is concerned are made according to the above method or by that method with minor variations well known in the peptide synthesis art. For example:

```
Synthesis of [Thr30]PP2-36 (SEQ ID No: 6)
In general side group protection is standard
Fmoc except for:
Arg =                    Fmoc Arg(Pbf)-OH Asn, Gln =               Fmoc Asn(Trt)-OH Thr, Ser, Asp, Glu, Tyr = tButyl Ala-Ser 22-23 =          Fmoc AlaSer
                         pseudoproline
```

Summary of Analytical Data for the Peptides Based on PP2-36:—

| SEQ ID No: | Structure | Molecular formula | Mw | Measured Mass m/z | Rt min | Purity % | Analytical method |
|---|---|---|---|---|---|---|---|
| 4 | [Ala30]-PP$_{2-36}$ | C181 H278 N52 O54 S | 4078.6 | 4053.7 | 14.0 | 96.9 | A |
| 6 | [Thr30]-PP$_{2-36}$ | C182 H280 N52 O55 S | 4108.6 | 4084.6 | 13.9 | 93.8 | A |
| 8 | [Asn30]-PP$_{2-36}$ | C182 H279 N53 O55 S | 4121.6 | 4098.6 | 14.0 | 90.1 | A |
| 10 | [Gln30]-PP$_{2-36}$ | C183 H281 N53 O55 S | 4135.6 | 4113.0 | 13.9 | 85.0 | A |
| 14 | [Glu10,Leu17,Thr30]-PP$_{2-36}$ | C184 H284 N52 O55 | 4104.6 | 4084.5 | 14.4 | 92.0 | A |
| 12 | [Glu10]-PP$_{2-36}$ | C184 H284 N52 O54 S2 | 4152.7 | 4132.2 | 14.3 | 93.7 | A |
| 16 | [Nle17,Nle30]-PP$_{2-36}$ | C185 H285 N52 O54 | 4101.6 | 4081.6 | 14.8 | 96.0 | A |
| 18 | [Glu10,Nle17,Nle30]-PP$_{2-36}$ | C186 H287 N52 O54 | 4115.6 | 44094.5 | 14.8 | 98.8 | A |

| Analytical HPLC method A | |
|---|---|
| Column = | Vydac C18 Peptide-Protein column, 250 × 4.6 mm |
| Buffer A = | 0.05% TFA in water |
| Buffer B = | 0.05% TFA in 100% MeCN |
| Gradient = | 0% B to 60% B in 20 min |
| Flow rate = | 1.00 mL/min |
| Wavelength = | 215 nm |

Mass spectroscopy=MALDI-TOF with gentisic acid or acyanohydroxy cinnamic acid as matrix.

Alternative HPLC analytical methods can be used, for example:—

| Analytical HPLC method B | |
|---|---|
| Column = | Phenomenix Jupiter C18, 250 × 4.6 mm & Guard cartridge |
| Buffer A = | 0.05% TFA in water |
| Buffer B = | 0.05% TFA in 100% MeCN |
| Gradient = | 0% B to 100% B in 30 min |
| Flow rate = | 1.00 mL/min |
| Wavelength = | 220 nm |

Biological Assays and Results
I. In Vitro Assays to Determine Peptide Potency
Human Y2 Receptor Potency Assay Potency of the test compounds on the human Y2 receptor is determined by performing dose-response experiments in COS-7 cells transiently transfected with the human Y2 receptor as well as a promiscuous G protein, Gqi5 which ensures that the Y2 receptor couples through a Gq pathway leading to an increase in inositol phosphate turnover.

Phosphatidylinositol turnover—One day after transfection COS-7 cells are incubated for 24 hours with 5 µCi of [3H]-myo-inositol (Amersham, PT6-271) in 1 ml medium supplemented with 10% fetal calf serum, 2 mM glutamine and 0.01 mg/ml gentamicin per well. Cells are washed twice in buffer, 20 mM HEPES, pH 7.4, supplemented with 140 mM NaCl, 5 mM KCl, 1 mM $MgSO_4$, 1 mM $CaCl_2$, 10 mM glucose, 0.05% (w/v) bovine serum; and are incubated in 0.5 ml buffer supplemented with 10 mM LiCl at 37 C for 30 min. After stimulation with various concentrations of peptide for 45 min at 37 C, cells are extracted with 10% ice-cold perchloric acid followed by incubation on ice for 30 min. The resulting supernatants are neutralized with KOH in HEPES buffer, and the generated [3H]-inositol phosphate are purified on Bio-Rad AG 1-X8 anion-exchange resin and counted in a beta counter. Determinations are made in duplicates. EC50 values were calculated using a standard pharmacological data handling software, Prism 3.0 (graphpad Sofware, San Diego, USA).

Human Y4 Receptor Potency Assay

Protocol as for the Y2 potency assay, except that human Y4-transformed COS-7 cells are used.

Human Y1 Receptor Potency Assay

Protocol as for the Y2 potency assay, except that human Y1-transformed COS-7 cells are used.

Human Y5 Receptor Potency Assay

Protocol as for the Y2 potency assay, except that human Y5-transformed COS-7 cells are used The results of testing NPY, PYY, PYY3-36, PP, $PP_{2-36}$ and eight of the agonists of the invention in the above potency assays are given in Table 2:

TABLE 2

| Peptide | hY2 EC50 nM | S.E.M. | n | hY4 EC50 nM | S.E.M. | n | hY1 EC50 nM | S.E.M. | n |
|---|---|---|---|---|---|---|---|---|---|
| NPY | 1.5 | 0.5 | 11 | 167 | 56 | 7 | 1.7 | 0.3 | 15 |
| PYY | 0.23 | 0.06 | 8 | 34 | 5 | 6 | 0.6 | 0.1 | 5 |
| PYY(3-36) | 0.33 | 0.05 | 21 | >1000 | — | 8 | 74 | 5 | 7 |
| PP | >1000 | — | 8 | 0.80 | 0.18 | 23 | 83 | 13 | 5 |
| PP(2-36) | >1000 | — | 8 | 0.74 | 0.08 | 9 | 296 | 23 | 7 |
| [Ala-30]-PP(2-36) | >1000 | | 3 | 1.04 | 0.15 | 3 | >1000 | — | 3 |
| [Thr-30]-PP(2-36) | >1000 | | 3 | 1.07 | 0.14 | 3 | >1000 | — | 3 |
| [Asn-30]-PP(2-36) | >1000 | | 3 | 3.05 | 0.28 | 3 | >1000 | — | 3 |
| [Gln-30]-PP(2-36) | >1000 | | 3 | 0.99 | 0.06 | 3 | >1000 | — | 3 |
| [Glu10;Leu17;Thr-30]-PP(2-36) | >1000 | | 3 | 1.07 | 0.05 | 3 | >1000 | — | 3 |
| [Glu-10]-PP(2-36) | >1000 | | 3 | 0.91 | 0.05 | 3 | 564 | 91 | 3 |
| [Nle17,Nle30]-PP(2-36) | >1000 | | 2 | 0.95 | 0.13 | 2 | 256 | 34 | 2 |
| [Glu10,Nle17,Nle30]-PP(2-36) | >1000 | | 2 | 0.79 | 0.14 | 2 | 263 | 33 | 2 |

"n" is the number of independent experiments.

In Vitro Assay to Determine Binding to Glycosamino Glycans (GAGS)

The ability of test compounds to bind to GAGs is monitored in an in vitro assay using immobilized heparin, i.e. a heparin agarose as affinity matrix. using either HiTrap heparin-Sepharose column (Amersham Pharmacia Biotech, Uppsala, Sweden) or heparin HPLC columns which are eluted with a 50-min linear gradient of 0-0.5 M NaCl in 50 mM sodium phosphate (pH 7.3) containing 2 mM DTT and 1 mM MgEDTA at a flow rate of 1 ml/min. For regeneration, the column was washed with 1 M NaCl in buffer A from 51-55 min.

The invention claimed is:

1. A Y4 receptor agonist peptide selected from the group consisting of:
   (i) [Glu10, Leu17,Thr30]PP$_{2-36}$ (SEQ ID NO:14);
   (ii) analogues of [Glu10, Leu17,Thr30]PP$_{2-36}$ (SEQ ID NO:14) which are N-terminally acetylated, PEGylated, or covalently coupled to a binding motif selected from the group consisting of a serum albumin binding motif, a glycosaminoglycan binding motif, and a helix inducing motif;
   (iii) [Glu10, Leu17,Thr30]PP (SEQ ID NO:15); and
   (iv) analogues of [Glu10, Leu17,Thr30]PP (SEQ ID NO:15) which are N-terminally acylated, PEGylated, or covalently coupled to a serum albumin binding motif, a glycosaminoglycan binding motif or a helix inducing motif.

2. The peptide of claim 1 which is acylated at its N-terminus.

3. The peptide of claim 2 which is acylated at its N-terminus with a carbon chain having from 2 to 24 carbon atoms.

4. The peptide of claim 2 which is acetylated at its N-terminus.

5. The peptide of claim 1 which comprises the binding motif.

6. The peptide of claim 5 which comprises the serum albumin binding motif, wherein the serum albumin binding motif is a lipophilic group.

7. The peptide of claim 6 wherein the lipophilic group comprises an optionally substituted, saturated or unsaturated, straight or branched hydrocarbon group of from 10 to 24 carbon atoms.

8. The peptide of claim 6 wherein a side chain of the peptide comprises the lipophilic group.

9. The peptide of claim 8 wherein the side chain is selected from the group consisting of:
   $CH_3(CH_2)_n CH(COOH)NH$—$CO(CH_2)_2 CONH$—, wherein n is an integer from 9 to 15,
   $CH_3(CH_2)_r CO$—$NHCH(COOH)(CH_2)_2 CONH$—, wherein r is an integer from 9 to 15,
   $CH_3(CH_2)_s CO$—$NHCH((CH_2)_2 COOH)CONH$—, wherein s is an integer from 9 to 15,
   $CH_3(CH_2)_m CONH$—, wherein m is an integer from 8 to 18,
   —$NHCOCH((CH_2)_2 COOH)NH$—$CO(CH_2)_p CH_3$, wherein p is an integer from 10 to 16,
   —$NHCO(CH_2)_2 CH(COOH)NH$—$CO(CH_2)_q CH_3$, wherein q is an integer from 10 to 16,
   $CH_3(CH_2)_n CH(COOH)NHCO$—, wherein n is an integer from 9 to 15,
   $CH_3(CH_2)_{p'} NHCO$—, wherein p' is an integer from 10 to 18,
   —$CONHCH(COOH)(CH_2)_4 NH$—$CO(CH_2)_m CH_3$, wherein m is an integer from 8 to 18,
   —$CONHCH(COOH)(CH_2)_4 NH$—$COCH((CH_2)_2 COOH)NH$—$CO(CH_2)_p CH_3$, wherein p is an integer from 10 to 16,
   —$CONHCH(COOH)(CH_2)_4 NH$—$CO(CH_2)_2 CH(COOH)NH$—$CO(CH_2)_q CH_3$, wherein q is an integer from 10 to 16, and
   a partly or completely hydrogenated cyclopentanophenanthrene skeleton.

10. The peptide of claim 8 wherein the lipophilic group-containing side chain is a $C_{12}$, $C_{14}$, $C_{16}$ or $C_{18}$ acyl group.

11. The peptide of claim 10 wherein the lipophilic group-containing side chain is a tetradecanoyl group.

12. The peptide of claim 5 which comprises the GAG binding motif.

13. The peptide of claim 12 wherein the GAG-binding motif comprises one or more of the amino acid sequences XBBXBX and XBBBXXBX, wherein B is a basic amino acid residue and X is any amino acid residue.

14. The peptide of claim 12 wherein the GAG-binding motif is concatameric or dendrimeric.

15. The peptide of claim 12 wherein the GAG-binding motif is a concatameric GAG binding motif and is Ala-Arg-Arg-Arg-Ala-Ala-Arg-Ala-Ala-Arg-Arg-Arg-Ala-Ala-Arg-Ala (SEQ ID NO:20).

16. The peptide of claim 5 which comprises the GAG binding motif, wherein the GAG binding motif is covalently linked to the C-terminus of the peptide.

17. The peptide of claim 5 wherein the GAG binding motif is covalently linked to the N-terminus of the peptide.

18. The peptide of claim 16 wherein the GAG-binding motif comprises one or more of the amino acid sequences XBBXBX and XBBBXXBX, wherein B is a basic amino acid residue and X is any amino acid residue.

19. The peptide of claim 16 wherein the GAG-binding motif comprises the amino acid sequence [XBBBXXBX]$_n$ where n is 1 to 5, B is a basic amino acid residue and X is any amino acid residue.

20. The peptide of claim 5 which is PEGylated.

21. The peptide of claim 5 which comprises the helix inducing motif.

22. The peptide of claim 21 wherein the helix inducing motif is covalently linked to the N-terminus of the peptide.

23. The peptide of claim 21 wherein the helix inducing motif comprises 4-20 amino acid residues selected from the group consisting of Ala, Leu, Ser, Thr, Tyr, Asn, Gln, Asp, Glu, Lys, Arg, His, Met, Orn, and amino acid residues of formula —NH—C(R1)(R2)-CO—, wherein R1 is hydrogen and R2 is optionally substituted C1-C6 alkyl, phenyl or phenylmethyl, or R1 and R2 taken together with the C atom to which they are attached form a cyclopentyl, cyclohexyl or cycloheptyl ring.

24. The peptide of claim 21 wherein the helix inducing motif comprises 4, 5 or 6 Lys residues.

25. The peptide of claim 22 which comprises an N-terminal Lys-Lys-Lys-Lys-Lys-Lys-Lys (SEQ ID NO:27) sequence.

26. A method of treatment of conditions responsive to activation of Y4 receptors, the method comprising administering to a patient in need thereof an effective amount of the peptide of claim 1.

27. The method of claim 26, wherein the condition treated is one for which regulation of energy intake or energy metabolism, control of intestinal secretion, decrease of gastro-intestinal tract motility, or decrease of rate of gastric emptying, is indicated.

28. The method of claim 27, wherein the condition treated is obesity or overweight, or a condition in which obesity or overweight is considered a contributory factor.

29. The method of claim 28 wherein the condition treated is selected from the group consisting of inflammatory bowel disease, bulimia, bulimia nervosa, Syndrome X (metabolic syndrome), diabetes, type 2 diabetes mellitus, Non Insulin Dependent Diabetes Mellitus (NIDDM), hyperglycemia, insulin resistance, impaired glucose tolerance, cardiovascular disease, hypertension, atherosclerosis, coronary artery disease, myocardial infarction, peripheral vascular disease, stroke, thromboembolic disease, hypercholesterolemia, hyperlipidemia, gallbladder disease, osteoarthritis, sleep apnea, a reproductive disorder, breast cancer, prostate cancer, and colon cancer.

30. The method of claim 26 wherein the patient is in a fasted state.

31. The method of claim 26, wherein the condition treated is diarrhoea or hyper-secretion from intestinal stomia.

32. The method of claim 26, wherein the condition treated is nausea or emesis.

33. The method of claim 26 wherein the condition of nausea or emesis treated is one arising from or anticipated to arise from treatment with another pharmaceutical agent.

34. The method of claim 26 wherein the peptide comprises a GAG-binding motif.

35. The method of claim 26 wherein the peptide comprises a serum-binding motif.

36. The method of claim 26 wherein the peptide is PEGylated.

37. The method of claim 26, wherein the peptide is administered to a patient via a parenteral route.

38. The peptide of claim 3 which comprises an N-terminal N—(N'-tetradecanoyl)-gammaglutamoyl group.

39. The method of claim 37 wherein the parenteral route is selected from the group consisting of subcutaneous, intramuscular, intravenous, nasal, transdermal and buccal administration.

40. The peptide of claim 1 which is PEGylated.

41. The peptide of claim 5 which comprises the serum albumin binding motif.

42. The peptide of claim 16 wherein the GAG binding motif is linked directly to the C-terminus.

43. The peptide of claim 16 wherein the GAG binding motif is linked to the C-terminus via a linker.

44. The peptide of claim 17 wherein the GAG binding motif is linked directly to the N-terminus of the peptide.

45. The peptide of claim 17 wherein the GAG binding motif is linked to the N-terminus via a linker.

46. The peptide of claim 17 wherein the GAG-binding motif comprises one or more of the amino acid sequences XBBXBX and XBBBXXBX, wherein B is a basic amino acid residue and X is any amino acid residue.

47. The peptide of claim 17 wherein the GAG-binding motif comprises the amino acid sequence $[XBBBXXBX]_n$ where n is 1 to 5, B is a basic amino acid residue and X is any amino acid residue.

48. The peptide of claim 20 which is PEGylated with a PEG which is a polyethylene glycol or a polyethylene oxide having a molecular weight of at most about 20 kDa.

49. The peptide of claim 21 wherein the helix inducing motif is covalently linked to the C-terminus of the peptide.

50. The peptide of claim 49 wherein the helix inducing motif is linked directly to the C-terminus of the peptide.

51. The peptide of claim 49 wherein the helix inducing motif is linked to the C-terminus of the peptide via a linker.

52. The peptide of claim 22 wherein the helix inducing motif is linked directly to the N-terminus of the peptide.

53. The peptide of claim 22 wherein the helix inducing motif is linked to the N-terminus of the peptide via a linker.

54. The Y4 receptor agonist peptide [Glu10, Leu17, Thr30]$PP_{2-36}$ (SEQ ID NO:14).

55. The Y4 receptor agonist peptide [Glu10, Leu17, Thr30]PP (SEQ ID NO:15).

56. The method of claim 26 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

57. The method of claim 27 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

58. The method of claim 28 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

59. The method of claim 29 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

60. The method of claim 30 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

61. The method of claim 31 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

62. The method of claim 32 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

63. The method of claim 39 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

64. The method of claim 34 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

65. The method of claim 35 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

66. The method of claim 36 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

67. The method of claim 36 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

68. The peptide of claim 38 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

69. The method of claim 39 wherein the Y4 receptor agonist peptide is [Glu10, Leu17, Thr30]$PP_{2-36}$ (SEQ ID NO:14) or [Glu10, Leu17, Thr30]PP (SEQ ID NO:15).

* * * * *

SEQUENCE LISTING

<160> NUMBER OF SEQ ID NOS: 27

<210> SEQ ID NO 1
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 1

Tyr Pro Ser Lys Pro Asp Asn Pro Gly Glu Asp Ala Pro Ala Glu Asp
 1               5                  10                  15

```
Met Ala Arg Tyr Tyr Ser Ala Leu Arg His Tyr Ile Asn Leu Ile Thr
            20                  25                  30

Arg Gln Arg Tyr
        35

<210> SEQ ID NO 2
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 2

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 3
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 3

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
        35

<210> SEQ ID NO 4
<211> LENGTH: 35
<212> TYPE: PRT
<213> ORGANISM: Artificial Sequence
<220> FEATURE:
<223> OTHER INFORMATION: Y4 receptor agonist peptide

<400> SEQUENCE: 4

Pro Leu Glu Pro Val Tyr Pro Gly Asp Asn Ala Thr Pro Glu Gln Met
1               5                   10                  15

Ala Gln Tyr Ala Ala Asp Leu Arg Arg Tyr Ile Asn Ala Leu Thr Arg
            20                  25                  30

Pro Arg Tyr
        35

<210> SEQ ID NO 5
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 5

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Ala Leu Thr
            20                  25                  30
```

Arg Pro Arg Tyr
        35

<210> SEQ ID NO 6
<211> LENGTH: 35
<212> TYPE: PRT
<213> ORGANISM: Artificial Sequence
<220> FEATURE:
<223> OTHER INFORMATION: Y4 receptor agonist peptide

<400> SEQUENCE: 6

Pro Leu Glu Pro Val Tyr Pro Gly Asp Asn Ala Thr Pro Glu Gln Met
1               5                   10                  15

Ala Gln Tyr Ala Ala Asp Leu Arg Arg Tyr Ile Asn Thr Leu Thr Arg
            20                  25                  30

Pro Arg Tyr
        35

<210> SEQ ID NO 7
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 7

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Thr Leu Thr
            20                  25                  30

Arg Pro Arg Tyr
        35

<210> SEQ ID NO 8
<211> LENGTH: 35
<212> TYPE: PRT
<213> ORGANISM: Artificial Sequence
<220> FEATURE:
<223> OTHER INFORMATION: Y4 receptor agonist peptide

<400> SEQUENCE: 8

Pro Leu Glu Pro Val Tyr Pro Gly Asp Asn Ala Thr Pro Glu Gln Met
1               5                   10                  15

Ala Gln Tyr Ala Ala Asp Leu Arg Arg Tyr Ile Asn Asn Leu Thr Arg
            20                  25                  30

Pro Arg Tyr
        35

<210> SEQ ID NO 9
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 9

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Asn Leu Thr
            20                  25                  30

Arg Pro Arg Tyr
        35

-continued

```
<210> SEQ ID NO 10
<211> LENGTH: 35
<212> TYPE: PRT
<213> ORGANISM: Artificial Sequence
<220> FEATURE:
<223> OTHER INFORMATION: Y4 receptor agonist peptide

<400> SEQUENCE: 10

Pro Leu Glu Pro Val Tyr Pro Gly Asp Asn Ala Thr Pro Glu Gln Met
1               5                   10                  15

Ala Gln Tyr Ala Ala Asp Leu Arg Arg Tyr Ile Asn Gln Leu Thr Arg
            20                  25                  30

Pro Arg Tyr
            35

<210> SEQ ID NO 11
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 11

Ala Pro Leu Glu Pro Val Tyr Pro Gly Asp Asn Ala Thr Pro Glu Gln
1               5                   10                  15

Met Ala Gln Tyr Ala Ala Asp Leu Arg Arg Tyr Ile Asn Glu Leu Thr
            20                  25                  30

Arg Pro Arg Tyr
            35

<210> SEQ ID NO 12
<211> LENGTH: 35
<212> TYPE: PRT
<213> ORGANISM: Artificial Sequence
<220> FEATURE:
<223> OTHER INFORMATION: Y4 receptor agonist peptide

<400> SEQUENCE: 12

Pro Leu Glu Pro Val Tyr Pro Gly Glu Asn Ala Thr Pro Glu Gln Met
1               5                   10                  15

Ala Gln Tyr Ala Ala Asp Leu Arg Arg Tyr Ile Asn Met Leu Thr Arg
            20                  25                  30

Pro Arg Tyr
            35

<210> SEQ ID NO 13
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 13

Ala Pro Leu Glu Pro Val Tyr Pro Gly Glu Asn Ala Thr Pro Glu Gln
1               5                   10                  15

Met Ala Gln Tyr Ala Ala Asp Leu Arg Arg Tyr Ile Asn Met Leu Thr
            20                  25                  30

Arg Pro Arg Tyr
            35

<210> SEQ ID NO 14
<211> LENGTH: 35
<212> TYPE: PRT
<213> ORGANISM: Artificial Sequence
```

<220> FEATURE:
<223> OTHER INFORMATION: Y4 receptor agonist peptide

<400> SEQUENCE: 14

Pro Leu Glu Pro Val Tyr Pro Gly Glu Asn Ala Thr Pro Glu Gln Leu
1               5                   10                  15

Ala Gln Tyr Ala Ala Asp Leu Arg Arg Tyr Ile Asn Thr Leu Thr Arg
            20                  25                  30

Pro Arg Tyr
        35

<210> SEQ ID NO 15
<211> LENGTH: 36
<212> TYPE: PRT
<213> ORGANISM: Artificial Sequence
<220> FEATURE:
<223> OTHER INFORMATION: Y4 receptor agonist peptide

<400> SEQUENCE: 15

Ala Pro Leu Glu Pro Val Tyr Pro Gly Glu Asn Ala Thr Pro Glu Gln
1               5                   10                  15

Leu Ala Gln Tyr Ala Ala Asp Leu Arg Arg Tyr Ile Asn Thr Leu Thr
            20                  25                  30

Arg Pro Arg Tyr
        35

<210> SEQ ID NO 16
<211> LENGTH: 35
<212> TYPE: PRT
<213> ORGANISM: Artificial Sequence
<220> FEATURE:
<223> OTHER INFORMATION: Y4 receptor agonist peptide
<220> FEATURE:
<221> NAME/KEY: misc_feature
<222> LOCATION: (1)..(35)
<223> OTHER INFORMATION: Xaa = Nle

<400> SEQUENCE: 16

Pro Leu Glu Pro Val Tyr Pro Gly Asp Asn Ala Thr Pro Glu Gln Xaa
1               5                   10                  15

Ala Gln Tyr Ala Ala Asp Leu Arg Arg Tyr Ile Asn Xaa Leu Thr Arg
            20                  25                  30

Pro Arg Tyr
        35

<210> SEQ ID NO 17
<211> LENGTH: 36
<212> TYPE: PRT
<213> ORGANISM: Artificial Sequence
<220> FEATURE:
<223> OTHER INFORMATION: Y4 receptor agonist peptide
<220> FEATURE:
<221> NAME/KEY: misc_feature
<222> LOCATION: (1)..(36)
<223> OTHER INFORMATION: Xaa = Nle

<400> SEQUENCE: 17

Ala Pro Leu Glu Pro Val Tyr Pro Gly Asp Asn Ala Thr Pro Glu Gln
1               5                   10                  15

Xaa Ala Gln Tyr Ala Ala Asp Leu Arg Arg Tyr Ile Asn Xaa Leu Thr
            20                  25                  30

Arg Pro Arg Tyr
        35

```
<210> SEQ ID NO 18
<211> LENGTH: 35
<212> TYPE: PRT
<213> ORGANISM: Artificial Sequence
<220> FEATURE:
<223> OTHER INFORMATION: Y4 receptor agonist peptide
<220> FEATURE:
<221> NAME/KEY: misc_feature
<222> LOCATION: (1)..(35)
<223> OTHER INFORMATION: Xaa = Nle

<400> SEQUENCE: 18

Pro Leu Glu Pro Val Tyr Pro Gly Glu Asn Ala Thr Pro Glu Gln Xaa
 1               5                  10                  15

Ala Gln Tyr Ala Ala Asp Leu Arg Arg Tyr Ile Asn Xaa Leu Thr Arg
            20                  25                  30

Pro Arg Tyr
        35

<210> SEQ ID NO 19
<211> LENGTH: 36
<212> TYPE: PRT
<213> ORGANISM: Artificial Sequence
<220> FEATURE:
<223> OTHER INFORMATION: Y4 receptor agonist peptide
<220> FEATURE:
<221> NAME/KEY: misc_feature
<222> LOCATION: (1)..(36)
<223> OTHER INFORMATION: Xaa = Nle

<400> SEQUENCE: 19

Ala Pro Leu Glu Pro Val Tyr Pro Gly Glu Asn Ala Thr Pro Glu Gln
 1               5                  10                  15

Xaa Ala Gln Tyr Ala Ala Asp Leu Arg Arg Tyr Ile Asn Xaa Leu Thr
            20                  25                  30

Arg Pro Arg Tyr
        35

<210> SEQ ID NO 20
<211> LENGTH: 16
<212> TYPE: PRT
<213> ORGANISM: Artificial Sequence
<220> FEATURE:
<223> OTHER INFORMATION: GAG binding motif

<400> SEQUENCE: 20

Ala Arg Arg Arg Ala Ala Arg Ala Ala Arg Arg Ala Ala Arg Ala
 1               5                  10                  15

<210> SEQ ID NO 21
<211> LENGTH: 24
<212> TYPE: PRT
<213> ORGANISM: Artificial Sequence
<220> FEATURE:
<223> OTHER INFORMATION: GAG binding motif

<400> SEQUENCE: 21

Ala Arg Arg Arg Ala Ala Arg Ala Ala Arg Arg Ala Ala Arg Ala
 1               5                  10                  15

Ala Arg Arg Arg Ala Ala Arg Ala
            20

<210> SEQ ID NO 22
<211> LENGTH: 59
<212> TYPE: PRT
<213> ORGANISM: Artificial Sequence
<220> FEATURE:
```

<223> OTHER INFORMATION: Y4 receptor agonist peptide

<400> SEQUENCE: 22

Ala Arg Arg Arg Ala Ala Arg Ala Ala Arg Arg Ala Ala Arg Ala
1               5                   10                  15

Ala Arg Arg Ala Ala Arg Ala Pro Leu Glu Pro Val Tyr Pro Gly
                20                  25                  30

Asp Asn Ala Thr Pro Glu Gln Met Ala Gln Tyr Ala Asp Leu Arg
            35                  40                  45

Arg Tyr Ile Asn Ala Leu Thr Arg Pro Arg Tyr
        50                  55

<210> SEQ ID NO 23
<211> LENGTH: 8
<212> TYPE: PRT
<213> ORGANISM: Artificial Sequence
<220> FEATURE:
<223> OTHER INFORMATION: GAG binding motif

<400> SEQUENCE: 23

Ala Arg Arg Arg Ala Ala Arg Ala
1               5

<210> SEQ ID NO 24
<211> LENGTH: 63
<212> TYPE: PRT
<213> ORGANISM: Artificial Sequence
<220> FEATURE:
<223> OTHER INFORMATION: Y4 receptor agonist peptide

<400> SEQUENCE: 24

Ala Arg Arg Arg Ala Ala Ala Arg Ala Ala Arg Arg Ala Ala
1               5                   10                  15

Arg Ala Ala Arg Arg Arg Ala Ala Ala Arg Ala Tyr Pro Ile Lys Pro
                20                  25                  30

Glu Ala Pro Gly Glu Asp Ala Lys Pro Glu Glu Leu Asn Arg Tyr Tyr
            35                  40                  45

Ala Ser Leu Arg His Tyr Leu Asn Ala Val Thr Arg Gln Arg Tyr
        50                  55                  60

<210> SEQ ID NO 25
<211> LENGTH: 41
<212> TYPE: PRT
<213> ORGANISM: Artificial Sequence
<220> FEATURE:
<223> OTHER INFORMATION: Helix-inducing peptide

<400> SEQUENCE: 25

Lys Lys Lys Lys Lys Lys Pro Leu Glu Pro Val Tyr Pro Gly Asp Asn
1               5                   10                  15

Ala Thr Pro Glu Gln Met Ala Gln Tyr Ala Asp Leu Arg Arg Tyr
                20                  25                  30

Ile Asn Ala Leu Thr Arg Pro Arg Tyr
            35                  40

<210> SEQ ID NO 26
<211> LENGTH: 27
<212> TYPE: PRT
<213> ORGANISM: Artificial Sequence
<220> FEATURE:
<223> OTHER INFORMATION: GAG binding domain

<400> SEQUENCE: 26

```
Ala Arg Arg Arg Ala Ala Ala Arg Ala Ala Arg Arg Arg Ala Ala Ala
1               5                   10                  15

Arg Ala Ala Arg Arg Ala Ala Ala Arg Ala
            20                  25

<210> SEQ ID NO 27
<211> LENGTH: 7
<212> TYPE: PRT
<213> ORGANISM: Artificial Sequence
<220> FEATURE:
<223> OTHER INFORMATION: helix-inducing peptide

<400> SEQUENCE: 27

Lys Lys Lys Lys Lys Lys Lys
1               5
```